(12) United States Patent
Hoeg et al.

(10) Patent No.: US 9,182,577 B2
(45) Date of Patent: Nov. 10, 2015

(54) VARIABLE DIRECTION OF VIEW INSTRUMENT WITH DISTAL IMAGE SENSOR

(75) Inventors: Hans David Hoeg, Arcadia, CA (US);
John C. Tesar, Tucson, AZ (US);
Nathan Jon Schara, Pasadena, CA (US); Eric L. Hale, Altadena, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1733 days.

(21) Appl. No.: 11/336,212

(22) Filed: Jan. 20, 2006

(65) Prior Publication Data

US 2006/0252995 A1 Nov. 9, 2006

Related U.S. Application Data

(60) Provisional application No. 60/646,203, filed on Jan. 21, 2005.

(51) Int. Cl.
| | |
|---|---|
| A62B 1/04 | (2006.01) |
| H04N 7/18 | (2006.01) |
| H04N 5/232 | (2006.01) |
| G02B 13/22 | (2006.01) |
| A61B 1/00 | (2006.01) |
| A61B 1/05 | (2006.01) |
| G02B 23/24 | (2006.01) |
| G02B 26/08 | (2006.01) |
| A61B 1/005 | (2006.01) |

(52) U.S. Cl.
CPC ............ *G02B 13/22* (2013.01); *A61B 1/00096* (2013.01); *A61B 1/00183* (2013.01); *A61B 1/05* (2013.01); *A61B 1/051* (2013.01); *G02B 23/243* (2013.01); *G02B 23/2423* (2013.01); *G02B 26/0883* (2013.01); *A61B 1/0051* (2013.01)

(58) Field of Classification Search
None
See application file for complete search history.

(56) References Cited

U.S. PATENT DOCUMENTS

| | | | |
|---|---|---|---|
| 2,764,149 A | 9/1956 | Sheldon | |
| 3,856,000 A | 12/1974 | Chikama | |
| 4,074,306 A | 2/1978 | Kakinuma et al. | |
| 4,253,447 A | 3/1981 | Moore et al. | |
| 4,598,980 A * | 7/1986 | Doi et al. | 359/735 |
| 4,697,577 A | 10/1987 | Forkner | |
| 4,720,178 A * | 1/1988 | Nishioka et al. | 359/431 |
| 4,868,644 A * | 9/1989 | Yabe et al. | 348/76 |
| 4,890,159 A | 12/1989 | Ogiu | |
| 4,916,534 A * | 4/1990 | Takahashi et al. | 348/67 |
| 4,988,172 A * | 1/1991 | Kanamori et al. | 359/654 |
| 5,166,787 A | 11/1992 | Irion | |
| 5,762,603 A | 6/1998 | Thompson | |
| 6,256,155 B1 * | 7/2001 | Nagaoka | 359/753 |
| 6,371,909 B1 | 4/2002 | Hoeg et al. | |
| 6,500,115 B2 | 12/2002 | Krattiger et al. | |
| 6,560,013 B1 | 5/2003 | Ramsbottom | |
| 6,648,817 B2 * | 11/2003 | Schara et al. | 600/173 |
| 6,731,845 B1 | 5/2004 | Gerdt | |
| 6,788,861 B1 * | 9/2004 | Utsui et al. | 385/119 |
| 2001/0031912 A1 | 10/2001 | Adler | |
| 2002/0068853 A1 * | 6/2002 | Adler | 600/160 |

* cited by examiner

*Primary Examiner* — Lin Ye
*Assistant Examiner* — Euel Cowan
(74) *Attorney, Agent, or Firm* — Whitmyer IP Group LLC

(57) ABSTRACT

A viewing instrument having a variable direction of view is disclosed generally comprising a shaft, a sensor mounted in the distal end of the shaft such that the image plane of the sensor is substantially parallel to the longitudinal axis of the shaft, and a reflecting element that rotates about an axis substantially perpendicular to the longitudinal axis of the shaft. In some embodiments, a negative lens is mounted adjacent the reflecting element, and in certain embodiments, a positive lens is positioned adjacent the image sensor.

14 Claims, 11 Drawing Sheets

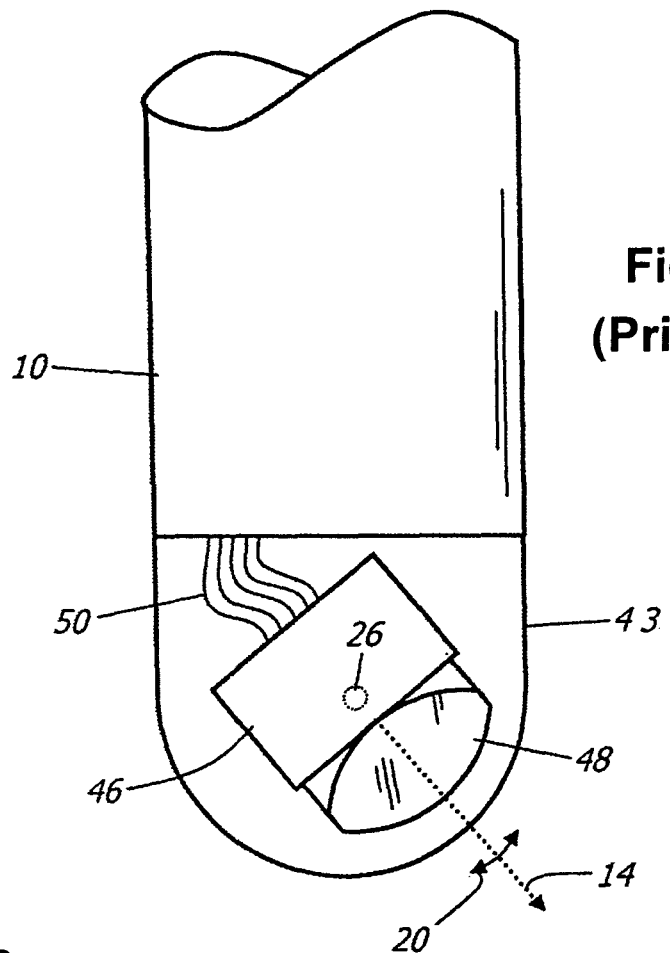
**Fig. 3A
(Prior Art)**
**Fig. 3B
(Prior Art)**
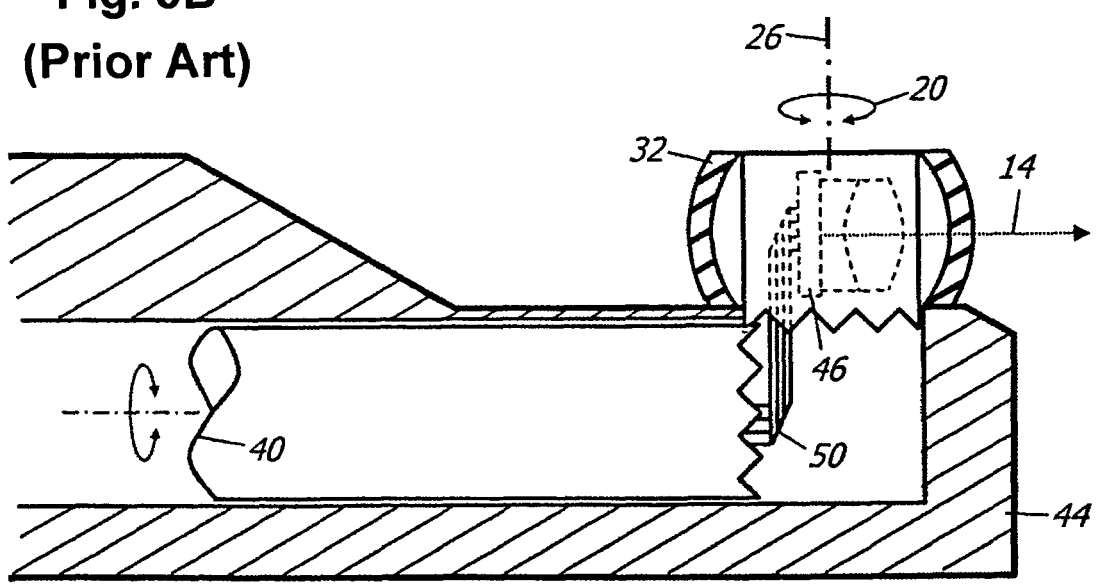

VARIABLE DIRECTION OF VIEW INSTRUMENT WITH DISTAL IMAGE SENSOR

CROSS-REFERENCE TO RELATED APPLICATIONS

This patent application claims the benefit of, under Title 35, United States Code, Section 119(e), U.S. Provisional Patent Application No. 60/646,203, filed Jan. 21, 2005.

FIELD OF THE INVENTION

The present invention relates to an apparatus for obtaining wide angles of view in small areas, such as a surgical site in a patient's body. More specifically, the invention relates to a viewing instrument, such as an endoscope, with a variable direction of view and a sensor in its distal end.

BACKGROUND OF THE INVENTION

Viewing instruments, such as endoscopes, are generally well known in the art. Generally, an endoscope is a medical device for insertion into a body passageway or cavity that enables an operator to view and/or perform certain surgical procedures at a site inside a patient's body. As is known, endoscopes may be either rigid or flexible, and generally include a long tubular member equipped with, for example, some type of system for transmitting images to the user, and in some cases, a working channel for a surgical instrument. The endoscope has a proximal end that remains external to the patient, from which the operator can view the site and/or manipulate a surgical instrument, and a distal end having an endoscope tip for insertion into the body cavity of the patient.

Traditionally, these instruments have used relay optics, such as rod lenses, fiber optic bundles, or relay lenses to transmit the images from inside the body cavity of the patient to the user's eye, located at the proximal end of the endoscope, or to a camera likewise connected to the scope for subsequent display on a monitor and/or storage on an image capture device.

These traditional arrangements suffer from a number of disadvantages. First, though systems for designing, constructing, and assembling relay systems have been around for some time, these systems continue to be costly, to be time-consuming, and to demand specialized expertise. Additionally, relay systems typically employ a large number of optical components, which must be precisely fabricated and positioned in order to achieve satisfactory image quality. Finally, image degradation is inevitable with such assemblies due to the fact that the light reflecting from the viewing objects must pass through a series of optical surfaces, as back-reflection, stray light, lens surface roughness, inaccuracies in lens curvatures, and slight lens misalignments all serve to reduce image quality.

Therefore, in order to attempt to circumvent these drawbacks, various designs have been proposed. For example, it has been suggested to use an endoscope with a miniature television tube located in its distal tip, such as the design disclosed in U.S. Pat. No. 2,764,149 to Sheldon. Likewise, other designs with distal imaging devices have been described in U.S. Pat. No. 4,074,306 to Kakinuma et al. and U.S. Pat. No. 4,253,447 to Moore et al. However, while such distal imager designs are effective for flexible and fixed-angle rigid endoscopes, they have, thus far, not worked well for endoscopes with a variable direction of view.

Examples of variable direction of view scopes are disclosed in U.S. Pat. No. 3,856,000 to Chikama et al., U.S. Pat. No. 4,697,577 to Forkner, U.S. Pat. No. 6,371,909 to Hoeg, et al., U.S. Pat. No. 6,500,115 to Krattiger et al., and U.S. Pat. No. 6,560,013 to Ramsbottom. The operating principles of such a scope are illustrated schematically in FIG. 1. A variable direction of view endoscope includes a shaft 10 having a proximal end 12. Such an endoscope has a view vector 14 with an attendant view field 16 having at least two degrees of freedom 18, 20. The first degree of freedom 18 permits rotation of the view vector 14 about the longitudinal axis 22 of the shaft 10, which allows the view vector 14 to scan in a latitudinal direction 24. The second degree of freedom 20 permits rotation of the view vector 14 about an axis 26 perpendicular to the longitudinal axis 22, which allows the view vector 14 to scan in a longitudinal direction 28. A third degree of freedom 30 may also be available because it is usually possible to adjust the rotational orientation of the endoscopic image.

Referring to FIGS. 2A-B, the operating principles of a dual reflector variable direction of view scope are illustrated. A first prism 32 refracts incoming light along a path 34 to a second prism 36, which delivers the light to an optical relay system 38 housed by a hollow transmission shaft 40. The first prism 32 is pivotable about an axis 26 and can be actuated by the transmission shaft 40 through a gear 42 to scan in a plane normal to the page. This optical assembly is covered by a glass dome 43 and supported by a mechanical structure 44, which forms the distal portion of the endoscope.

Such scopes have been unable to employ a traditional optical relay system as efficiently as is possible due to the fact that, as illustrated, these scopes use movable reflecting/refracting elements to change the endoscopic line of sight, and therefore, require complex designs for the distal end of the endoscope such that the tip is capable of folding the optical path and accommodating a miniature transmission mechanism. As a result, less room is available for an optical relay system, the performance of which decreases as its cross-section decreases. Therefore, a variable direction of view endoscope will necessarily have an inferior image quality than a fixed-angle scope of the same diameter when employing a relay lens system.

However, as noted above, thus far, employing a distal imager in the endoscope tip (instead of using a relay system) in order to maintain good image quality has not yet been accomplished as effectively as is possible, as it has proved to be very challenging to do so while, at the same time, keeping the endoscope diameter small. Examples of such systems have been described in Hoeg, as well as, U.S. Pat. No. 5,762,603 to Thompson and U.S. Pat. No. 6,648,817 to Schara et al, which disclose variable direction of view scopes employing pivotable image sensors. However, such pan-tilt schemes are difficult to implement compactly.

A variable direction of view endoscope with a pivotable distal imager is illustrated in FIG. 3A. An electronic image sensor 46 is located at the tip of the scope shaft 10 and pivots about an axis 26. This arrangement requires too much room to be able to fit within standard diameters of a significant number of standard endoscopes because the sensor 46 requires integrated objective optics 48 and flexible cabling 50. Because the solid state imaging device requires a set of lenses between the object being viewed and the image plane of the sensor, this assembly must sweep out a large radius when pivoted, which is simply too large for many endoscopic applications. Additionally, the cabling 50 limits the available scan range. Additionally, the mechanisms required to support and actuate such pivotable sensors require some complexity. An alternative, similar design, illustrated in FIG. 3B, experiences these same disadvantages.

A few designs have been proposed employing a side-mounted, stationary camera in order to minimize the required space, such as those disclosed in U.S. Pat. No. 4,890,159 to Ogiu, U.S. Pat. No. 5,166,787 to Irion, and U.S. Patent Application Nos. 2001/0031912 and 2002/0068853 by Adler. However, while these designs may be space-efficient, none of these devices are able to provide the same viewing versatility that is currently possible by employing a mechanism that enables a variable direction of view.

What is desired, therefore, is a viewing instrument having a variable direction of view that minimizes image degradation. What is further desired is a viewing instrument having a variable direction of view that can be employed in a small diameter. What is also desired is a viewing instrument having a variable direction of view that maximizes the scan range of the instrument.

SUMMARY OF THE INVENTION

Accordingly, it is an object of the present invention to provide a viewing instrument having a variable direction of view that does not require a relay lens assembly.

It is a further object of the present invention to provide a viewing instrument having a variable direction of view that does not require a pivoting assembly that sweeps out a large radius.

It is yet another object of the present invention to provide a viewing instrument having a variable direction of view that does not require cabling that restricts the scan range.

It is still another object of the present invention to provide a viewing instrument having a variable direction of view that does not require a large number of optical components.

In order to overcome the deficiencies of the prior art and to achieve at least some of the objects and advantages listed, the invention comprises a viewing instrument having a variable direction of view, including a shaft having a distal end and a longitudinal axis, a sensor mounted in the distal end of the shaft, the sensor having an image plane substantially parallel to the longitudinal axis of the shaft, and a reflecting element located at the distal end of the shaft that receives incoming light and redirects the light onto the image plane of the sensor, wherein the element rotates about a rotational axis substantially perpendicular to the longitudinal axis of the shaft.

In some of these embodiments, the instrument further includes a negative lens located adjacent the reflecting element through which the incoming light is transmitted to the reflecting element, and a convex surface through which the redirected light is transmitted from the reflecting element onto the image plane of the sensor. In some embodiments, the convex surface is a first convex surface, and the instrument further includes a second lens located adjacent the image plane of the sensor, the second lens having a second convex surface through which the light transmitted through the first convex surface is transmitted to the image plane of the sensor. In certain embodiments, the instrument further includes an optical component located between the first convex surface and the second lens, through which the light transmitted through the first convex surface is transmitted to the second lens.

In another embodiment, the invention comprises a viewing instrument having a variable direction of view, including a shaft having a distal end and a longitudinal axis, a sensor mounted in the distal end of the shaft, the sensor having an image plane substantially parallel to the longitudinal axis of the shaft, and a reflecting assembly located at the distal end of the shaft that receives incoming light and redirects the light onto the image plane of the sensor, wherein the assembly includes a reflecting element that rotates about a rotational axis substantially perpendicular to the longitudinal axis of the shaft.

In yet another embodiment, the invention comprises a viewing instrument having a variable direction of view, including a shaft having a distal end and a longitudinal axis, a sensor mounted in the distal end of the shaft, the sensor having an image plane substantially parallel to the longitudinal axis of the shaft, and a reflecting assembly located at the distal end of the shaft that receives incoming light and redirects the light onto the image plane of the sensor, wherein the assembly includes a reflecting element that rotates about a rotational axis substantially perpendicular to the longitudinal axis of the shaft.

In some of these embodiments, the scope has a distal end, and further includes an optical component located at the distal end of the scope that receives incoming light and redirects the light onto the image plane of the sensor. In some embodiments, the instrument further includes an optical component that retrofocuses the incoming light. In certain embodiments, an optical component that transmits the redirected light onto the image plane of the sensor telecentrically.

BRIEF DESCRIPTION OF THE DRAWINGS

FIG. 3A is a top plan view of a variable direction of view endoscope employing a pivotable distal imager.

FIG. 3B is a side cross-sectional view of a variable direction of view endoscope employing a pivotable distal imager.

DETAILED DESCRIPTION OF THE INVENTION

Figure 1:
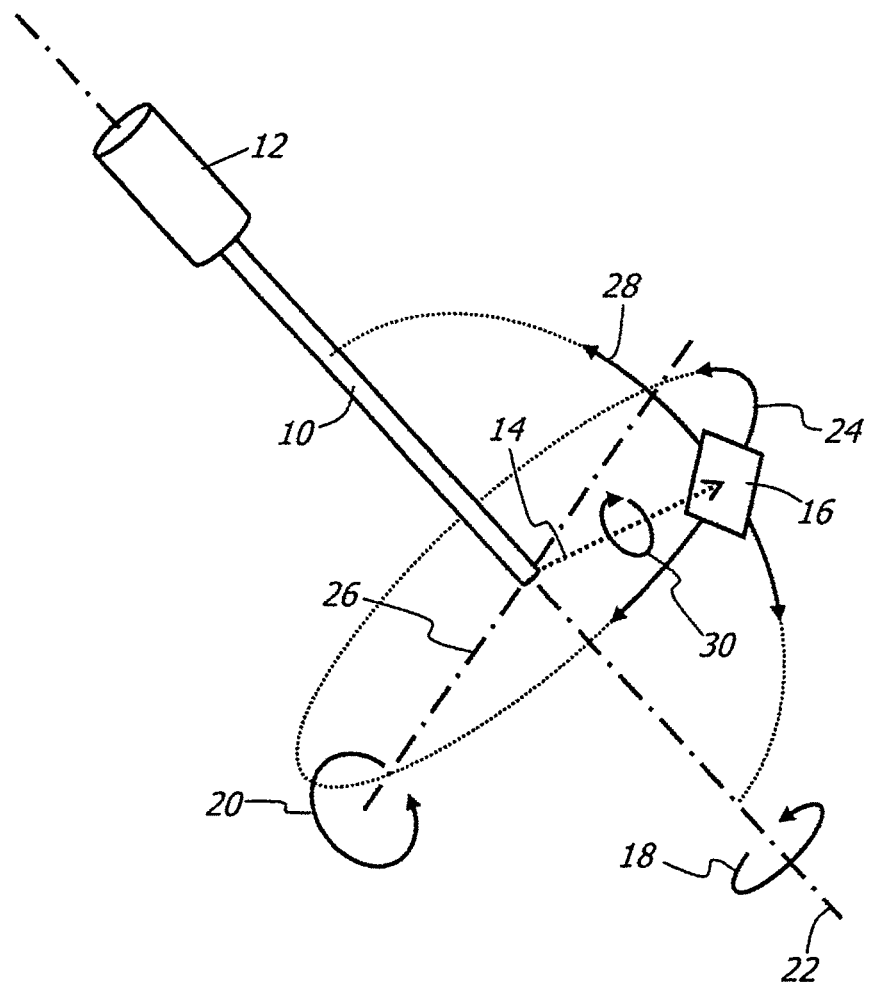
FIG. 1 is a schematic view of the operating principle of an endoscope with a variable direction of view.
Figure 2A:
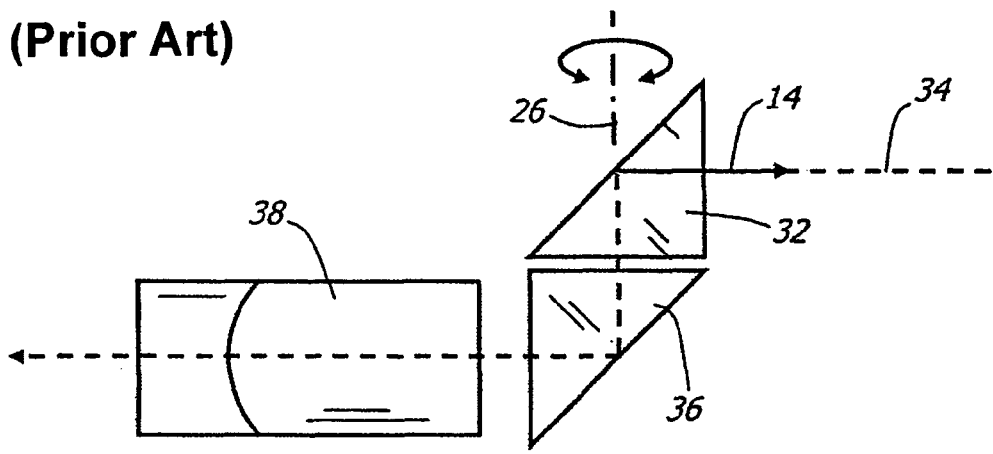
FIG. 2A is a schematic view of the optical path of a variable direction of view endoscope employing a relay lens system.
Figure 2B:
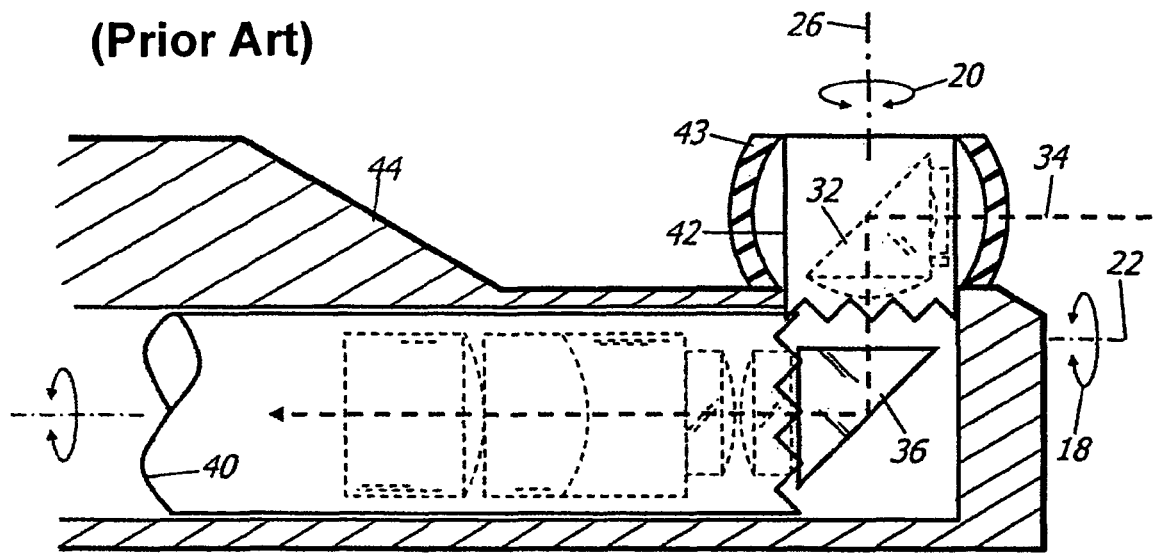
FIG. 2B is a side cross-sectional view of a variable direction of view endoscope employing a relay lens system.
Figure 4:
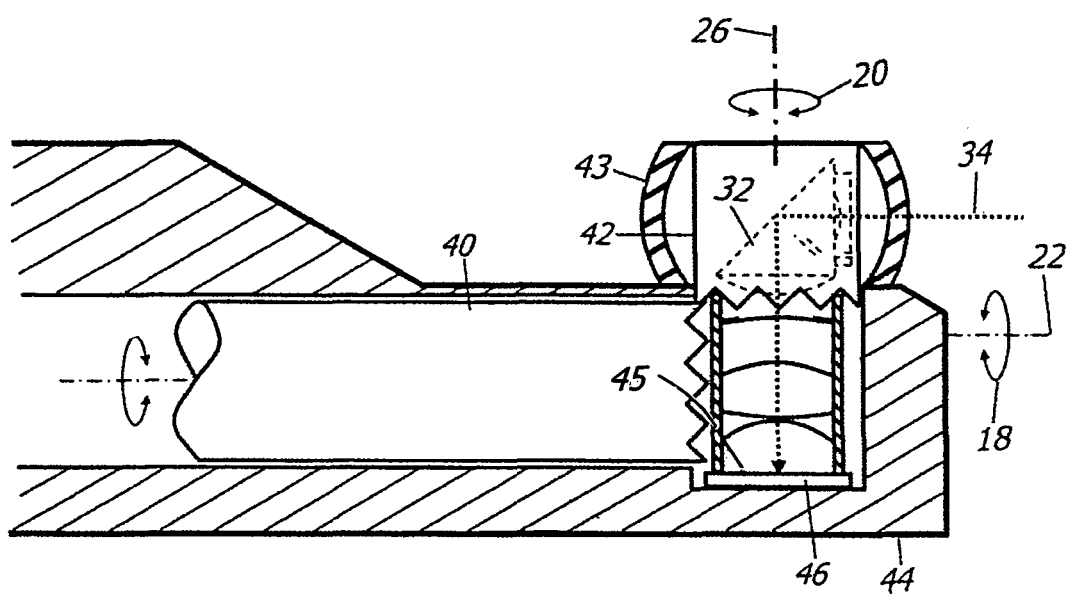
FIG. 4 is a side cross-sectional view of a variable direction of view endoscope employing an image sensor in accordance with the invention.

The basic components of one embodiment of a viewing instrument having a variable direction of view in accordance with the invention are illustrated in FIG. 4. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The instrument includes a shaft with a distal end 44 and a longitudinal axis 22, about which the endoscope may be rotated by the user to scan along the first degree of freedom 18. An optical assembly, which includes a reflecting element 32 for folding the optical path 34 of the assembly, as well as other optical components as further described below, is located at the shaft's distal end 44.

The reflecting element 32 is rotatable about a rotational axis 26 substantially perpendicular to the longitudinal axis 22 in order to scan along the second degree of freedom 20. The movement of the element 32 is powered by an actuator, which may, for example, include a transmission shaft 40 that drives a gear 42 in order to cause the element 32 to rotate and thereby scan in a plane normal to the rotational axis 26. The optical assembly is covered by a glass dome 43 and is supported by the distal portion 44 of the endoscope shaft 10. An image sensor 46 is mounted in the distal portion 44 such that the image plane 45 of the sensor 46 is substantially parallel to the longitudinal axis 22 of the shaft 10 (i.e., side-mounted).

Figure 5A:
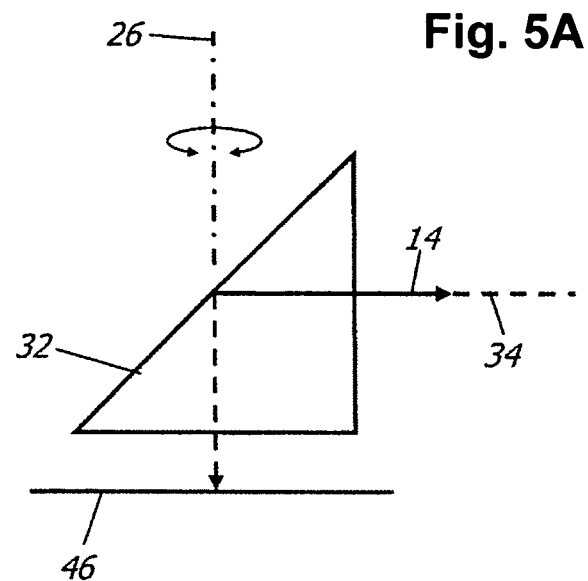
FIGS. 5A-H are side views showing additional detail of the image sensor of the endoscope of FIG. 4.
Figure 6:
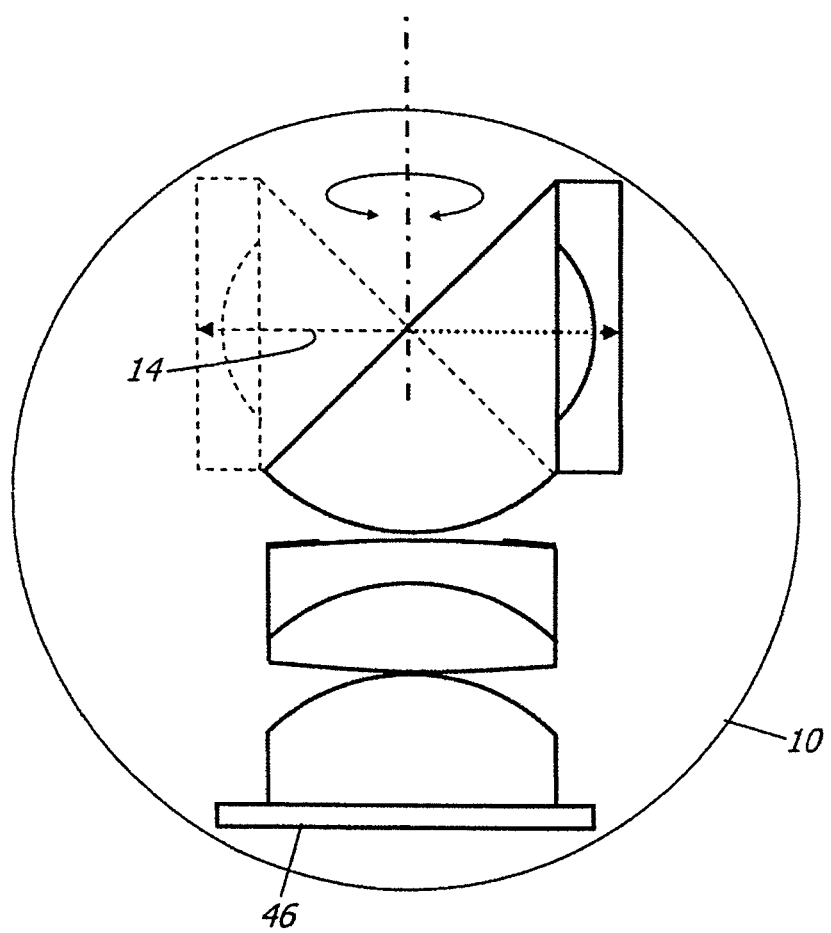
FIG. 6 is a schematic end view of the inside of the distal end of the endoscope of FIG. 4.

The reflecting element 32 may comprise any component for changing the optical axis of the optical train, further described below, in order to redirect the incoming light onto the image plane 45 of the sensor 46, such as, for example, a right-angled prism, as is illustrated in FIG. 5A. By employing an arrangement for folding the optical path in this way, the radius that must be swept out during rotation of the instrument's view vector 14 is reduced, as is more clearly illustrated in FIG. 6, showing an example objective-sensor assembly within the diameter of the scope shaft 10. Moreover, by allowing the imager 46 to remain stationary, problems associated with the flexing and/or rotating of electrical connections are also avoided.

Figure 5B:
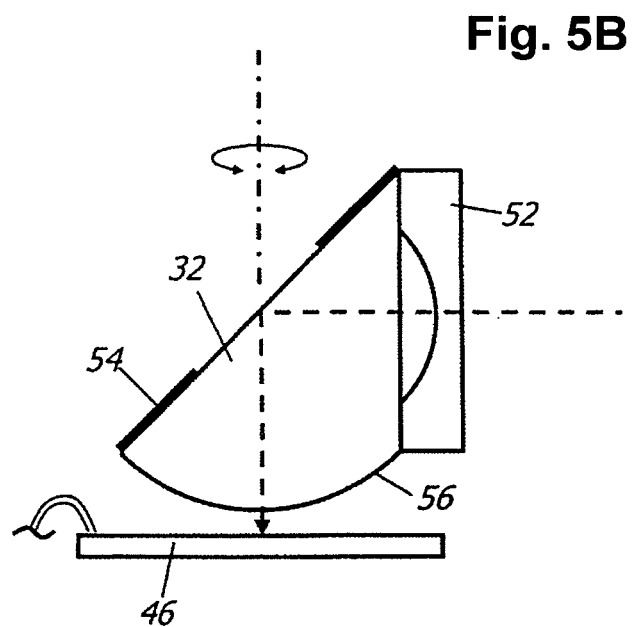

In order to properly implement this path-folding arrangement such that good image quality is maintained, the optical assembly may include various optical components. Referring to FIG. 5B, a negative lens 52, such as a plano-concave lens, is mounted adjacent the reflecting element 32. The lens 52 has an optical axis substantially perpendicular to the rotational axis of the reflecting element 32, and receives the incoming light and transmits it to the element 32, thereby retrofocusing the incoming light. The light is redirected through a convex surface 56, which may be an integral part of the element 32 or may, for example, be part of a separate plano-convex lens. An aperture stop 54 for limiting the diameter of the light is also provided, which may be placed towards the front or back of the lens train, depending on the types of glass and the particular lens curvatures used.

Figure 5C:
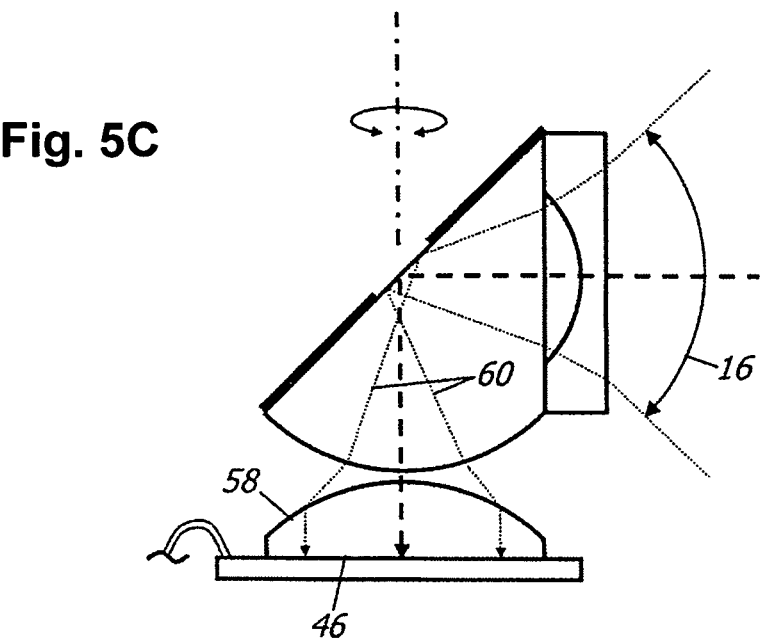
Figure 5D:
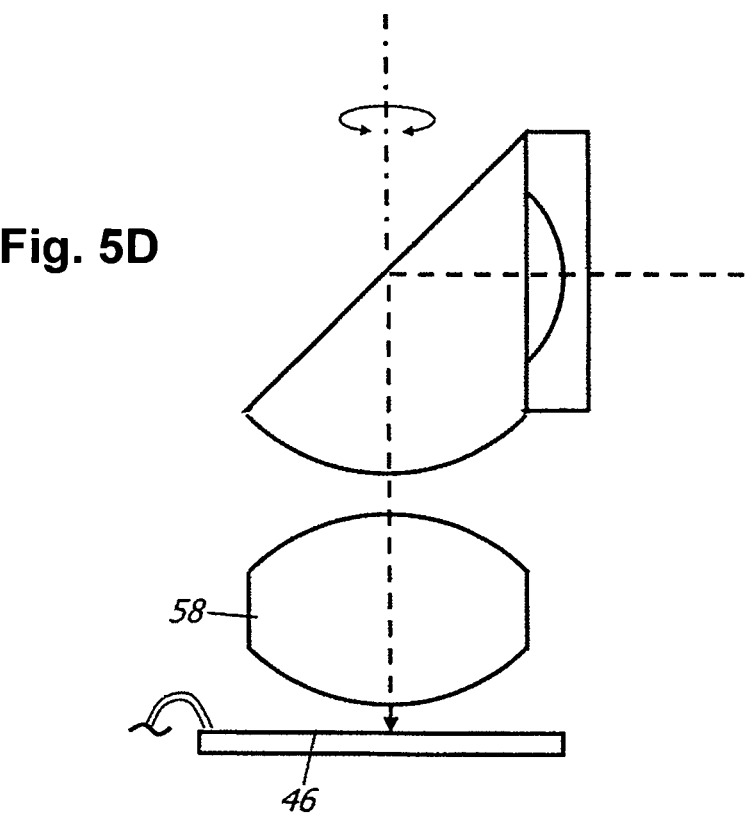

Referring to FIG. 5C, a second, positive lens 58 is located adjacent the sensor 46 and has an optical axis substantially perpendicular to the optical axis of the negative lens 52. The positive lens 58 receives the redirected light from the convex surface of the element 32 and transmits it to the image plane 45. The positive lens 58 may comprise, for example, a plano-convex lens, providing a second convex surface through which the light travels prior to reaching the sensor 46, transmitting the redirected light onto the image plane 45 telecentrically. Other positive lenses may be used, such as, for example, a double-convex lens as illustrated in FIG. 5D. As a result of such arrangements, the optical assembly provides a wide field of view 16 as well as telecentricity of the delimited chief rays 60 at the image plane 45.

Figure 5E:
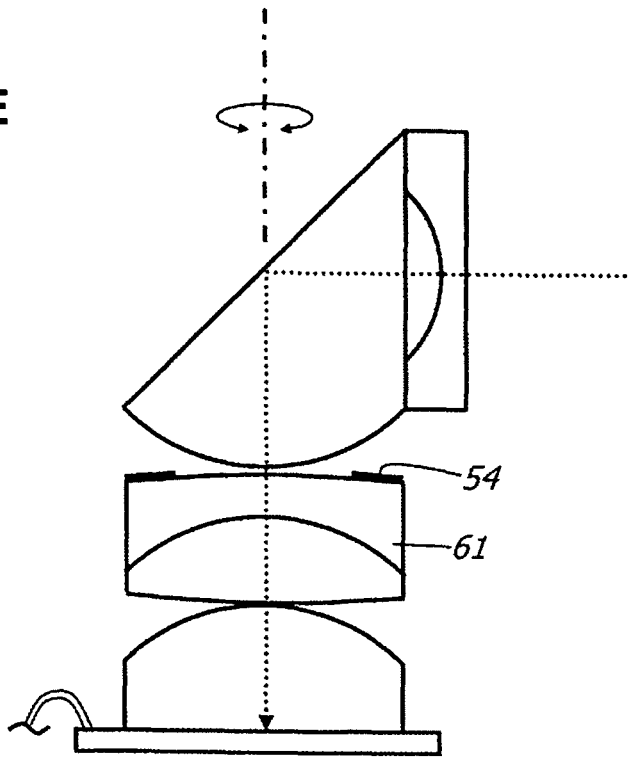
Figure 5F:
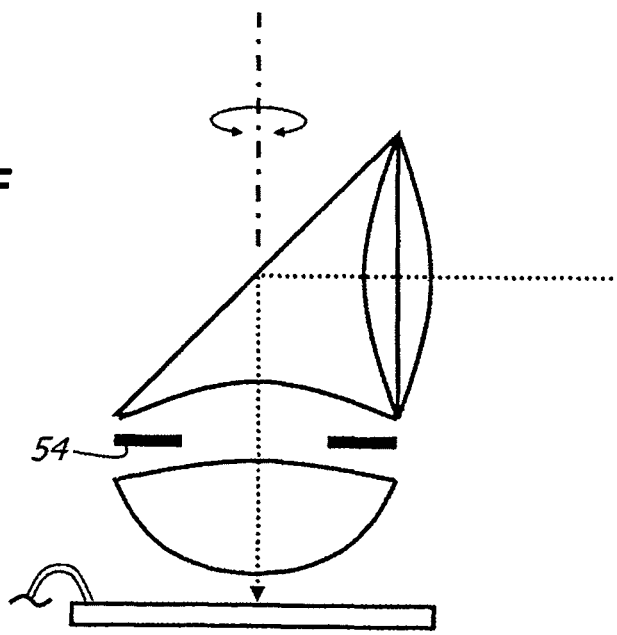
Figure 5G:
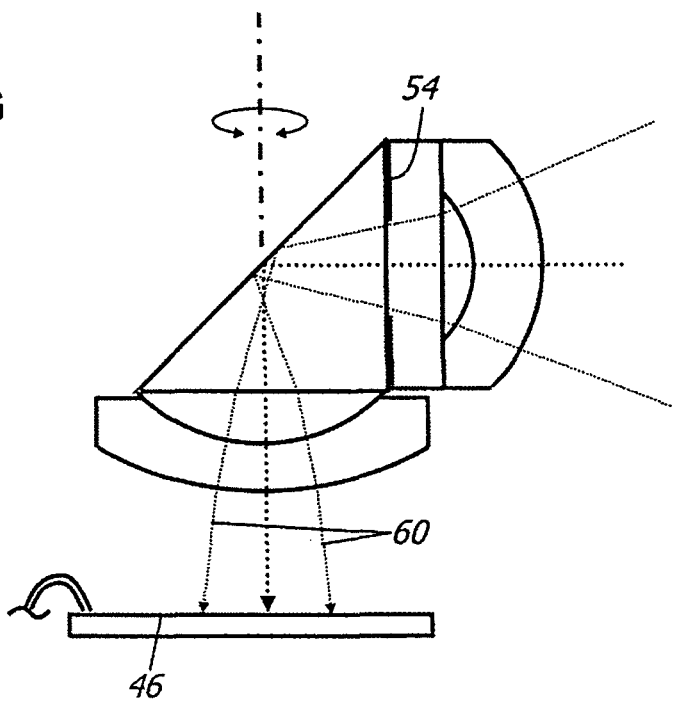
Figure 5H:
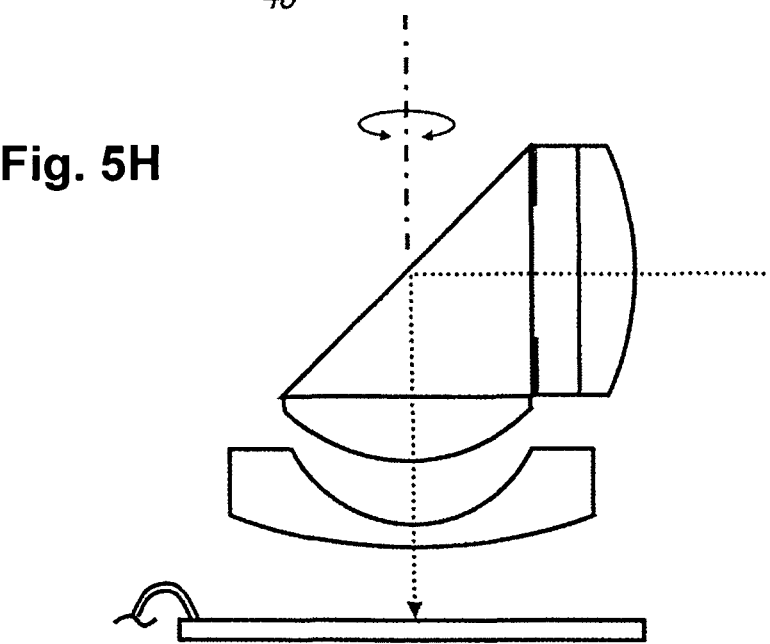

Referring to FIG. 5E, in some advantageous embodiments, an additional optical component 61 is located between the convex surface 56 and the second lens 58. For example, as illustrated, an achromatic doublet may be provided for color correction. Another example of the lens curvatures that may be employed is illustrated in FIG. 5F. Moreover, other arrangements are possible, such as the symmetric objective systems illustrated in FIG. 5G-H. In such arrangements, the incident and exiting light cones are more similar than in the optical assemblies described above. As shown in FIG. 5G, the chief rays 60 are not telecentric when arriving at the sensor plane 46, which is acceptable for certain types of sensors, and such arrangements may be particularly useful for certain applications because they are very compact.

Figure 7A:
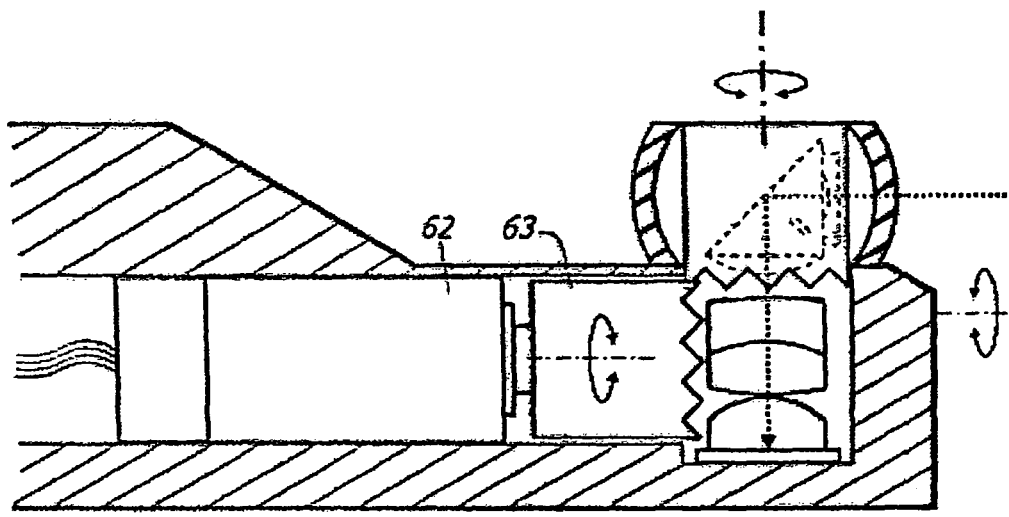
FIGS. 7A-C are side cross-sectional views showing additional detail of the actuators for rotating the reflecting element of FIG. 4.
Figure 7B:
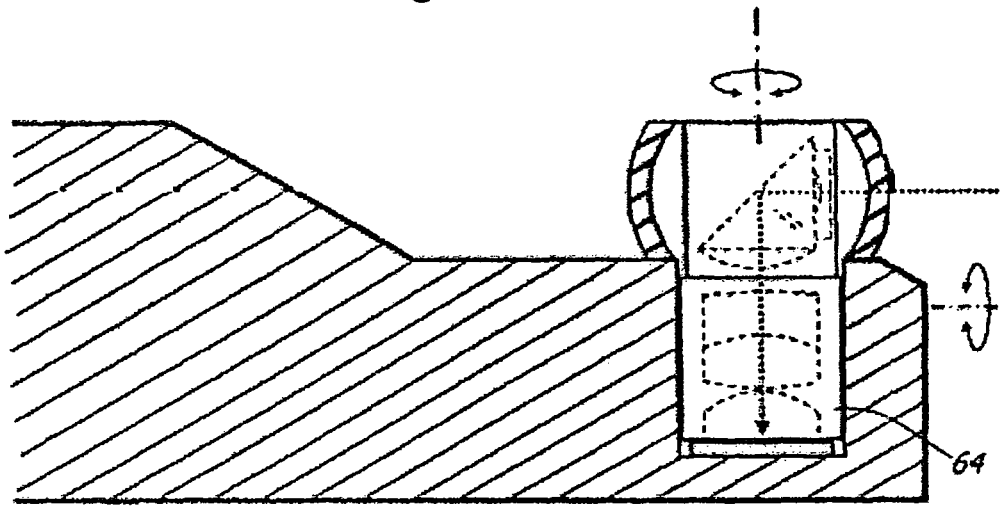
Figure 7C:
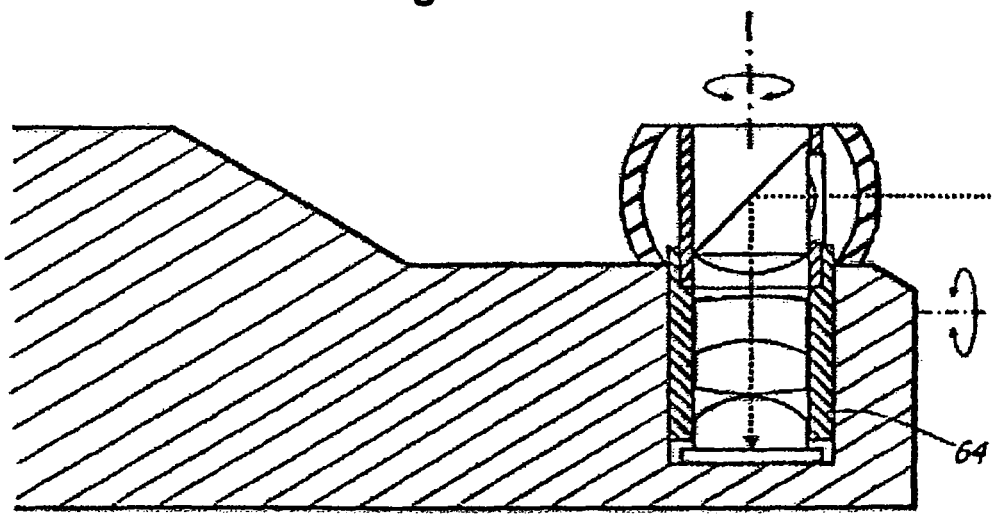

As shown in FIGS. 7A-C, other actuators for driving the rotation of the reflecting element 32 may also be employed. For example, as shown in FIG. 7A, in some embodiments, a distal motor 62 with a drive gear 63 is implemented. Alternatively, as illustrated in FIGS. 7B-C, a hollow-shaft direct drive motor 64 may be provided, which rotates the reflecting element 32 directly.

In certain embodiments, a reflecting assembly is provided that folds the optical path several times. As discussed above, a significant challenge for employing distal imagers is the reduced path length. Because the sensor 46 must be close to the very tip of the shaft 10 in order to not obstruct the actuator that rotates the element 32, the light's path from the point of entry into the scope to the sensor 46 is short. Typically, the angle of incidence onto an image sensor should be less than 15 degrees. However, it is difficult to convert a wide view field to a small angle of incidence over such a short distance. Accordingly, in certain advantageous embodiments, the optical path is extended by providing a reflecting assembly that folds the optical path more than once.

Figure 8:
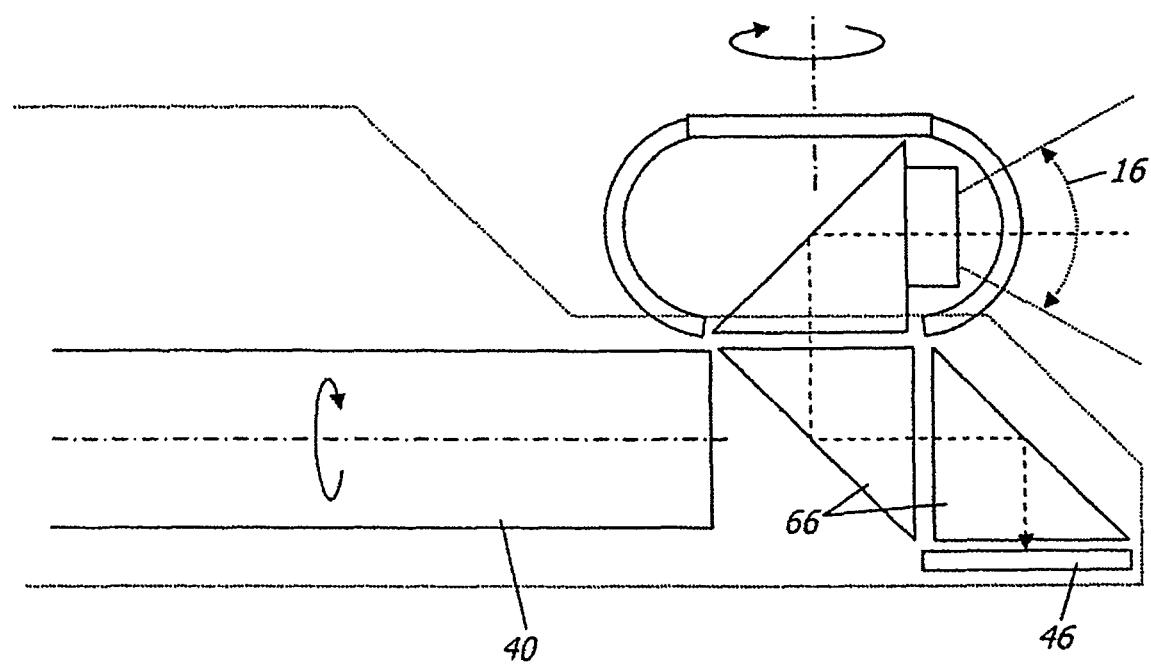
FIG. 8 is a schematic view of the endoscope of FIG. 4 employing a reflecting assembly for extending the optical path.

As shown in FIG. 8, two additional prisms 66 are employed to fold the optical path two additional times, thereby providing approximately 30% more path length while simultaneously keeping these optics and the sensor 46 out of the way of the transmission shaft 40. This type of arrangement allows the chief rays to be bent more gradually over a greater distance.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A viewing instrument having a variable direction of view, comprising:
   an endoscopic device comprising;
   a shaft having a distal end and a longitudinal axis;
   a sensor mounted in the distal end of said shaft, said sensor having an image plane substantially parallel to the longitudinal axis of said shaft; and
   a reflecting assembly for reducing the angle of incidence of incoming light onto the image plane of the sensor by increasing the path length travelled by the incoming light, comprising:
   a first reflecting element boated at the distal end of sad shaft that receives incoming light and redirects the light in a direction generally perpendicular to the longitudinal axis of said shaft and wherein said element rotates about a rotational axis substantially perpendicular to the longitudinal axis of said shaft;
   a second reflecting element that receives the light redirected by said first reflecting element and redirects the light in a direction generally parallel to the longitudinal axis of said shaft and toward the distal and of said shaft; and
   a third reflecting element that receives the light redirected by said second reflecting element and redirects the light onto the image plane of said sensor.

2. The viewing instrument of claim 1, wherein the reflecting element comprises a right-angled prism.

3. The viewing instrument of claim 1, further comprising:
a negative lens located adjacent said reflecting element through which the incoming light is transmitted to said reflecting element.

4. The viewing instrument of claim 3, wherein said negative lens has an optical axis substantially perpendicular to said rotational axis.

5. The viewing instrument of claim 1, wherein in reflective element includes an aperture stop.

6. The viewing instrument of claim 1, further comprising an actuator mounted in said shaft for rotating said reflecting element about said rotational axis.

7. The viewing instrument of claim 6, wherein said actuator comprises a drive shaft that rotates about said longitudinal axis, further comprising a gear driven by said rotating drive shaft and connected to said reflecting element.

8. The viewing instrument of claim 6, wherein said actuator comprises a motor arranged in said shaft and a drive gear rotated about said longitudinal axis by said motor, further comprising a second gear driven by said drive gear and coupled to said reflecting element.

9. The viewing instrument of claim 6, wherein said actuator comprises a hollow shaft motor that rotates about said rotational axis and is coupled to said reflecting element.

10. The viewing instrument of claim 1, wherein said shaft comprises an endoscope shaft.

11. The viewing instrument of claim 1, wherein said first, second, and third reflecting elements each comprise a right-angled prism.

12. The viewing instrument of claim 1, wherein said second reflecting element and said third reflecting element are arranged so that the path length traveled by the incoming light is approximately 30% more than if the incoming light were redirected from the first reflecting element directly to the image plane of said sensor.

13. The viewing instrument of claim 1, wherein said first, second, and third reflecting elements are arranged so that the angle of incidence of incoming light onto the image plane of the sensor is less than 15 degrees.

14. The viewing instrument of claim 6, wherein said second reflecting element is disposed between said actuator and said sensor in said shaft.

\* \* \* \* \*